United States Patent
Hsiung et al.

(10) Patent No.: US 12,311,103 B2
(45) Date of Patent: May 27, 2025

(54) PORTABLE OSCILLATOR OF POSITIVE EXPIRATORY PRESSURE HAVING CAPABILITY FOR OSCILLATING INDICATION

(71) Applicant: BESMED HEALTH BUSINESS CORP., New Taipei (TW)

(72) Inventors: Tao-Tsun Hsiung, New Taipei (TW); Xu-Xiang Wang, New Taipei (TW); I-Chen Tsai, New Taipei (TW)

(73) Assignee: BESMED HEALTH BUSINESS CORP., New Taipei (TW)

( * ) Notice: Subject to any disclaimer, the term of this patent is extended or adjusted under 35 U.S.C. 154(b) by 854 days.

(21) Appl. No.: 17/391,598

(22) Filed: Aug. 2, 2021

(65) Prior Publication Data

US 2022/0313930 A1    Oct. 6, 2022

(30) Foreign Application Priority Data

Mar. 30, 2021   (TW) ................. 110112048

(51) Int. Cl.
*A61M 16/00* (2006.01)
*A61B 5/087* (2006.01)
(Continued)

(52) U.S. Cl.
CPC ......... *A61M 16/0006* (2014.02); *A61B 5/087* (2013.01); *A61M 16/0866* (2014.02);
(Continued)

(58) Field of Classification Search
CPC .......... A61M 16/0006; A61M 16/0866; A61M 16/208; A61M 2016/0027;
(Continued)

(56) References Cited

U.S. PATENT DOCUMENTS 10,004,872 B1 *  6/2018  Gao ................ A61M 16/0866
2003/0234017 A1 * 12/2003  Pelerossi .......... A61M 16/205
                                                     128/201.28

FOREIGN PATENT DOCUMENTS

GB          2448212 A  * 10/2008  ........ A61M 16/0006

* cited by examiner

*Primary Examiner* — Rene T Towa
*Assistant Examiner* — Matthew Eric Ogles
(74) *Attorney, Agent, or Firm* — BACON & THOMAS, PLLC

(57) ABSTRACT

A portable oscillator of positive expiratory pressure having capability for oscillating indication, the portable oscillator of positive expiratory pressure comprises a shell, an oscillation element and an indicator element; the shell has a pressurized cavity, the oscillation element has a valve to close the pressurized cavity, the indicator element is used to respond an oscillating state of the oscillation element and a static state of the oscillation element; wherein the shell and the oscillation element are respectively provided with a first magnetic element and a second magnetic element; when an expiratory airflow through the pressurized cavity drives the oscillation element to rotate, the valve will separate from the pressurized cavity to release the pressure, a distance between the first magnetic element and the second magnetic element is simultaneously shortened to quickly respond to a repulsive force which is generated between the same poles, and therefore the oscillation element can be returned to an original position; when the valve recloses the pressurized cavity, the pressurized cavity will produce an exhalation resistance.

10 Claims, 16 Drawing Sheets

(51) Int. Cl.
*A61M 16/08* (2006.01)
*A61M 16/20* (2006.01)

(52) U.S. Cl.
CPC ......... *A61M 16/208* (2013.01); *A61B 5/0873* (2013.01); *A61M 2016/0027* (2013.01); *A61M 2205/0272* (2013.01); *A61M 2205/584* (2013.01)

(58) Field of Classification Search
CPC .... A61M 2205/0272; A61M 2205/584; A61M 16/049; A61M 2205/583; A61M 16/20; A61M 16/08; A61M 16/00; A61M 16/0015; A61M 16/0021; A61M 16/0024; A61M 16/0036; A61M 16/0039; A61M 16/0042; A61M 16/0075; A61M 16/0078; A63B 23/18; A61B 5/0871; A61B 5/087; A61B 5/0873; A61B 5/0876; A61B 5/095; A61B 5/08
See application file for complete search history.

PORTABLE OSCILLATOR OF POSITIVE EXPIRATORY PRESSURE HAVING CAPABILITY FOR OSCILLATING INDICATION

BACKGROUND OF THE INVENTION

1. Field of the Invention

The present invention relates to a portable oscillator of positive expiratory pressure, and the present invention relates in particular to a portable oscillator of positive expiratory pressure having capability for oscillating indication, the portable oscillator of positive expiratory pressure is provided with an oscillation element and a pressurized cavity. When a user exhales into the portable oscillator of positive expiratory pressure, an airflow of expiratory through the oscillation element and the pressurized cavity will produce an oscillating positive expiratory pressure therapy (hereafter referred to as "OPEP therapy"). Moreover, the portable oscillator of positive expiratory pressure can indicates an oscillating state of the oscillation element and a static state of the oscillation element.

2. Description of Related Art

An OPEP therapy is an airway clearance treatment. When a user actively exhales into an OPEP device, the OPEP device will provide an expiratory resistance to bring about a positive intrathoracic pressure, therefore the lung volume can be increased, and moreover the upper airway can be expanded. In particular, the positive expiratory pressure oscillation of the OPEP device can enhances the strength of ciliary beating, therefore the airway clearance effect will be better.

A prior-art is disclosed in U.S. Pat. No. 6,581,598, the prior-art disclosed a positive expiratory pressure device. When a user applies a positive expiratory air pressure at a patient input end (202), the air pressure is applied through an opening (326) against a cone (425) of a rocker assembly (400) which forms a closure of the opening (326); wherein the pressure of the patient expiratory will raise the cone (425) to cause the rocker assembly (400) to pivot about its pivot pins (460) thereby against a force of magnetic field which is between a magnet (350) carried on a pivotal magnet support (330) and a steel pin (450) carried on the rocker assembly (400). When the cone (425) moves upwardly, a tapered configuration of a tapered conical interior (325) of a coupling (322) increases the effective discharge area thereby decreasing the patient induced expiratory air pressure applied against the cone (425). When the magnetic force and the venturi effect of airflow overcome the air pressure applied to the cone (425), the cone (425) will again move downwardly into the tapered conical surface (325) momentarily closing off the expiratory air flow through the opening (326).

The patent family of the prior-art patent has German Patent No. DE60035328T2, European Patent No. EP1103287B1 and Spanish Patent No. ES2288832T3. During the positive expiratory pressure treatment of the user, the prior-art does not provide a visual incentive. Thus, the prior-art still requires improvement.

SUMMARY OF THE INVENTION

It is therefore an object of the invention to provide a portable oscillator of positive expiratory pressure having capability for oscillating indication, the portable oscillator of positive expiratory pressure comprises a shell, an oscillation element and an indicator element; the shell has a pressurized cavity, the oscillation element has a valve to close the pressurized cavity, the indicator element is used to respond an oscillating state of the oscillation element and a static state of the oscillation element; wherein the shell and the oscillation element are respectively provided with a first magnetic element and a second magnetic element; when an expiratory airflow through the pressurized cavity drives the oscillation element to rotate, the valve will separate from the pressurized cavity to release the pressure, a distance between the first magnetic element and the second magnetic element is simultaneously shortened to quickly respond to a repulsive force which is generated between the same poles, and therefore the oscillation element can be returned to an original position; when the valve recloses the pressurized cavity, the pressurized cavity will produce an exhalation resistance.

First advantages of the invention include the indicator element can displays an oscillating state of the oscillation element and a static state of the oscillation element, that will feed back a visual incentive effect to a user, and thereby increasing the success of OPEP therapy.

Second advantages of the invention include the return position of the oscillation element uses the repulsive force to return the position, wherein the repulsive force is responded from the same poles of the first magnetic element and the second magnetic element, and therefore the portable oscillator of positive expiratory pressure is less affected by gravity, the user can still uses the portable oscillator of positive expiratory pressure while lying in the hospital bed.

Third advantages of the invention include the first magnetic element and the second magnetic element can be respectively fixed by a package, thereby avoiding that the first magnetic element and the second magnetic element could contact with air and humidity, the invention will be better achieved in the product protection and the product life.

The above and other objects, features and advantages of the invention will become apparent from the following detailed description taken with the accompanying drawings.

DETAILED DESCRIPTION OF THE INVENTION

Figure 1:
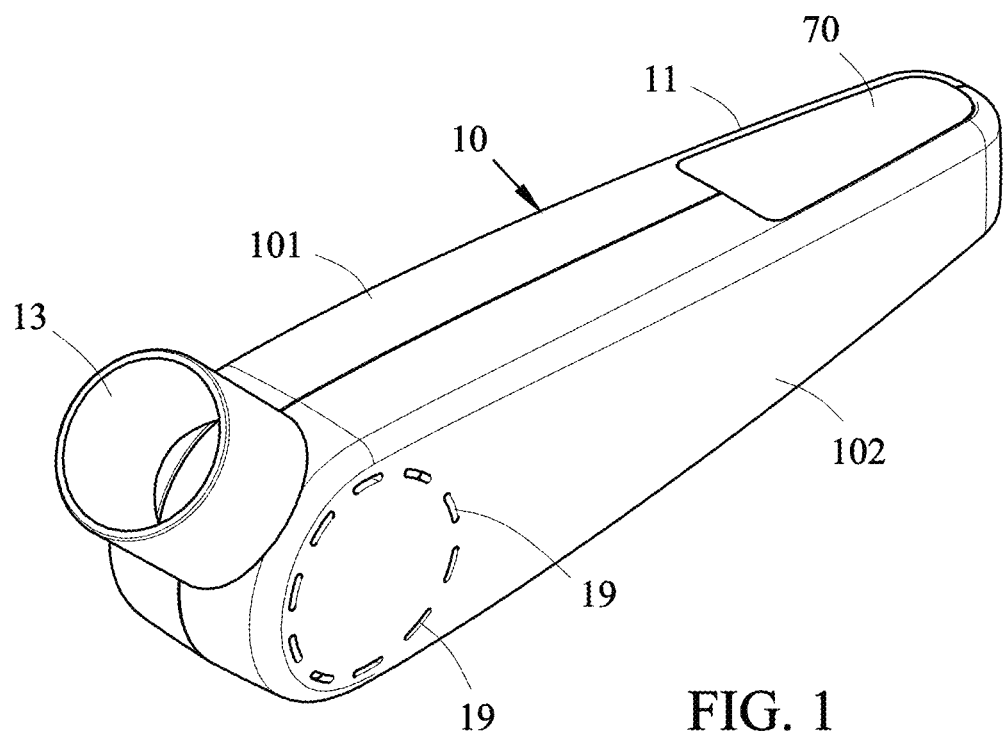
FIG. 1 is a perspective view showing a first preferred embodiment of the invention.
Figure 2:
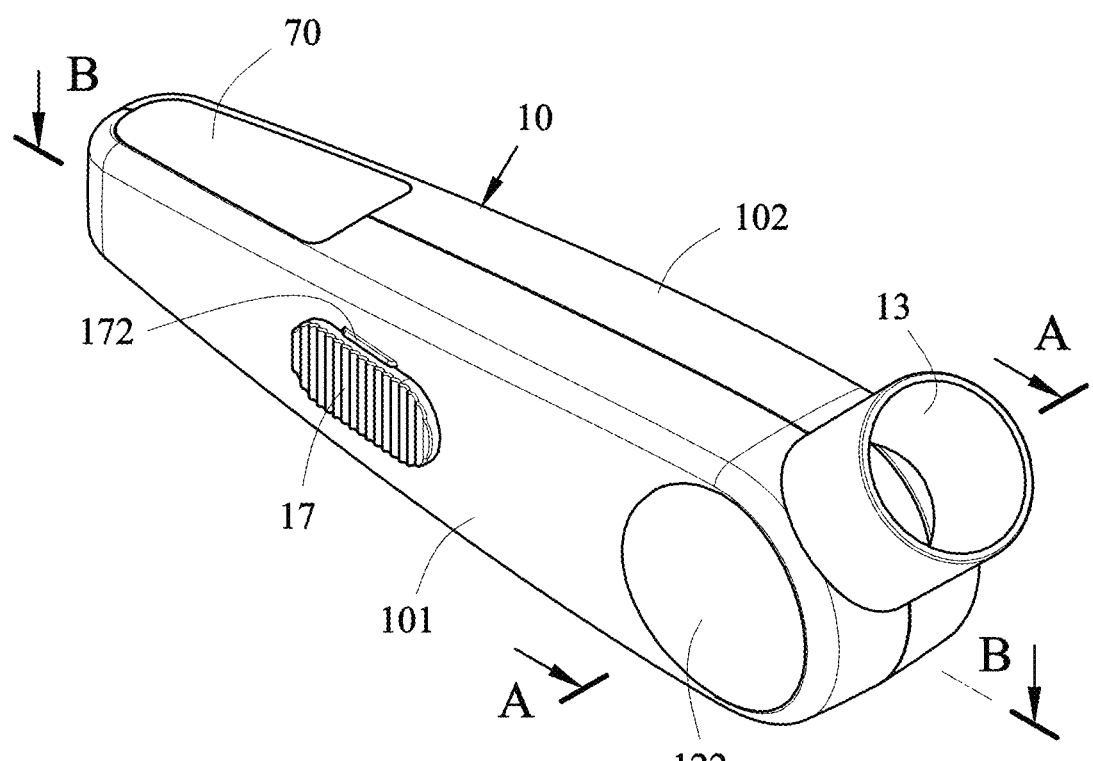
FIG. 2 is another perspective view showing the first preferred embodiment of the invention.
Figure 3:
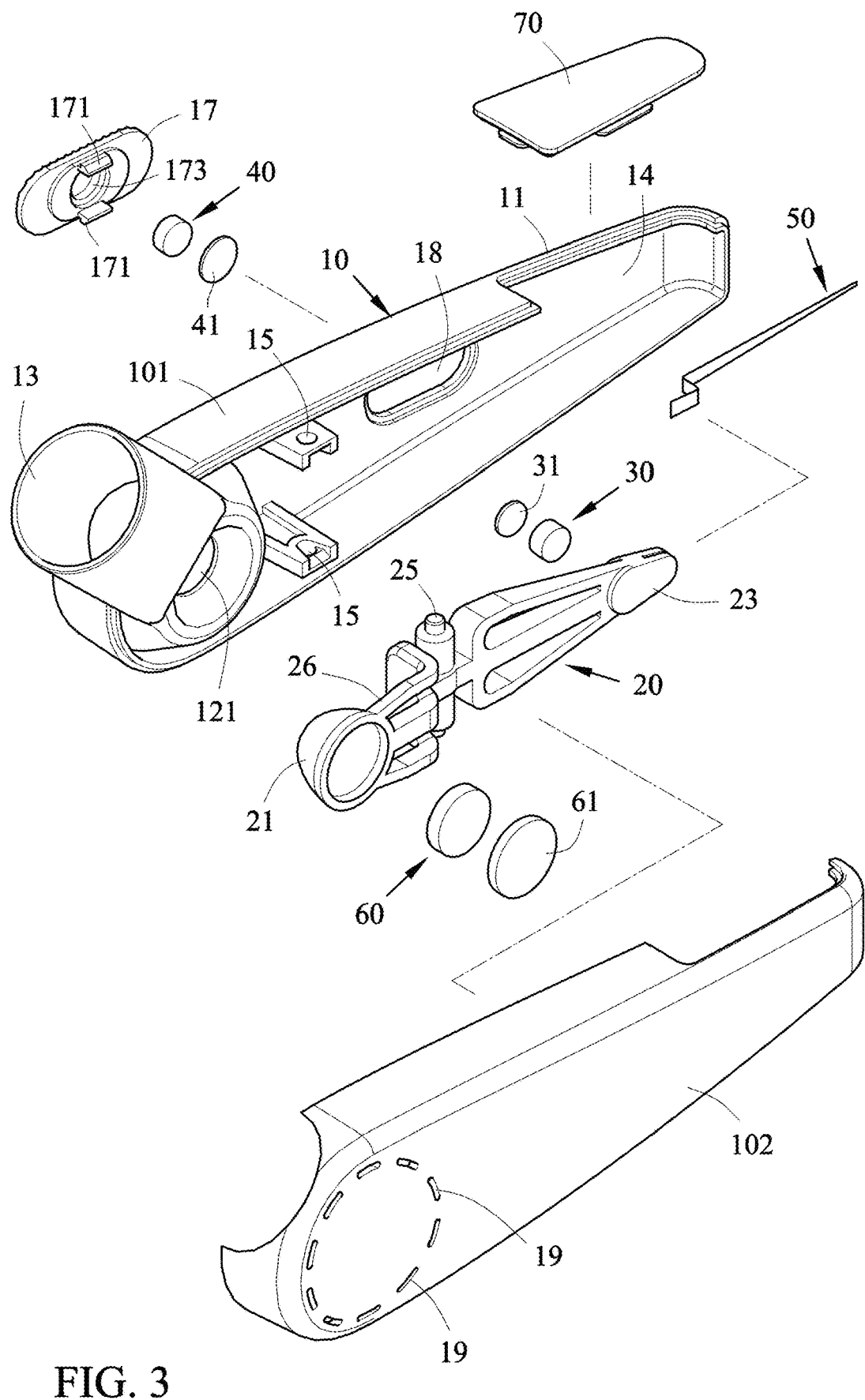
FIG. 3 is an exploded view showing the first preferred embodiment of the invention.
Figure 4:
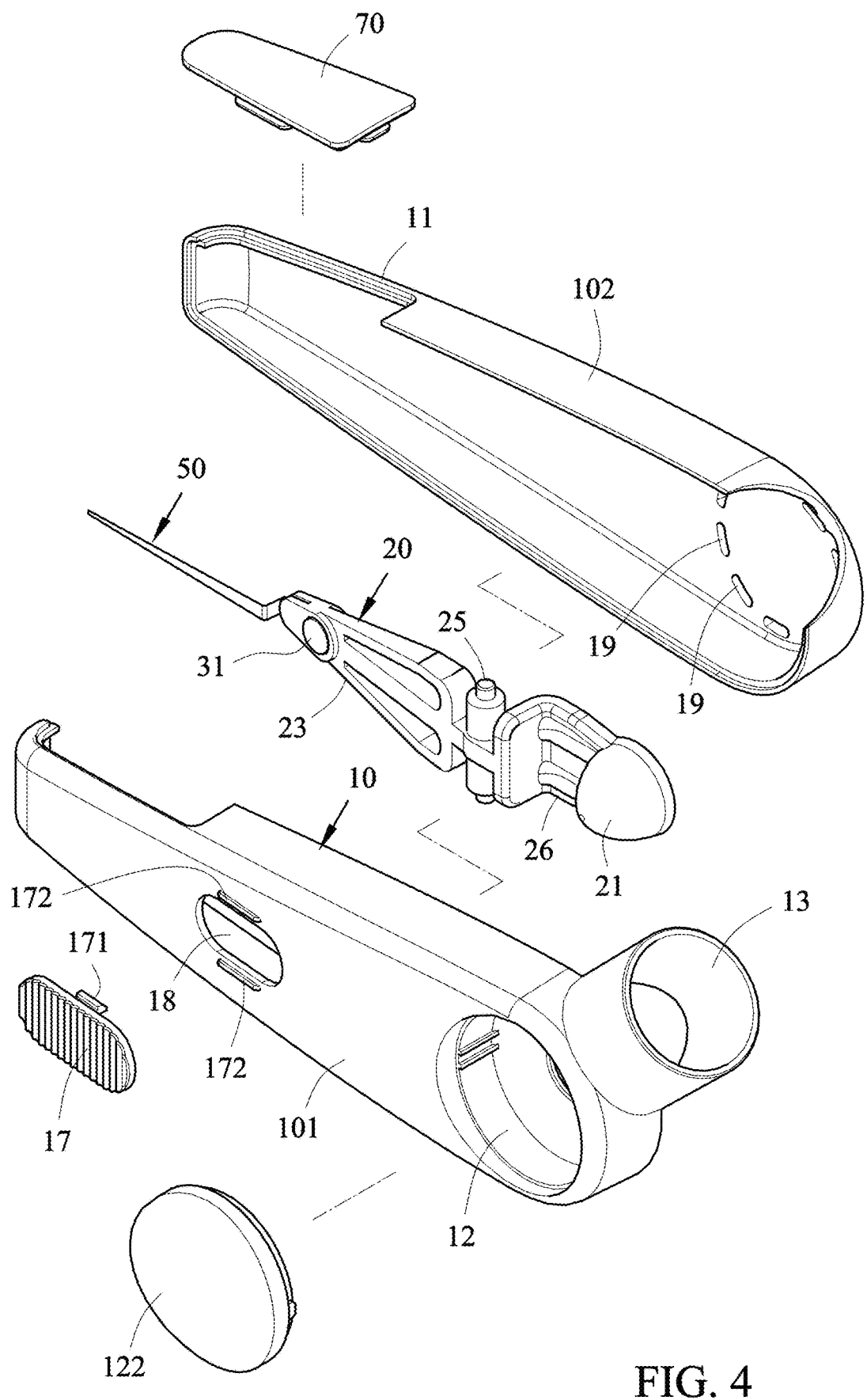
FIG. 4 is a partial exploded view showing the first preferred embodiment of the invention.

FIGS. 1 to 6A show a first preferred embodiment of the invention, a portable oscillator of positive expiratory pressure having capability for oscillating indication (hereafter referred to as "Portable device of OPEP") comprises a shell 10, an oscillation element 20, a first magnetic element 30, a second magnetic element 40 and an indicator element 50. The shell 10 has a pressurized cavity 12, the pressurized cavity 12 fluid communicates with an air inlet portion 13, the oscillation element 20 has a valve 21, and the oscillation element 20 is pivoted in the shell 10. The first magnetic element 30 is disposed on a first end 23 of the oscillation element 20, the second magnetic element 40 is disposed on the shell 10, the magnetic field lines of the first magnetic element 30 in a direction opposite to the direction of the magnetic field lines of the second magnetic element 40 (for example, a corresponding relationship of same pole repulsion is formed between the first magnetic element and the second magnetic element), and therefore the valve 21 tends to close an opening 121 of the pressurized cavity 12. The indicator element 50 is located at the first end 23 of the oscillation element 20, the indicator element 50 is used to respond an oscillating state of the oscillation element 20 and a static state of the oscillation element 20; wherein an expiratory airflow generates a forward thrust in the pressurized cavity 12 to drive the oscillation element 20 to rotate, and therefore a distance between the first magnetic element 30 and the second magnetic element 40 is shortened to generate a reverse thrust (for example, a repulsive force of the same poles is responded by the distance shortening of the first magnetic element 30 and the second magnetic element 40). When the valve 21 separates from the opening 121 of the pressurized cavity 12 in a moment, the forward thrust is reduced, and therefore the reverse thrust can drives the oscillation element 20 to return to an original position. When the valve 21 closes the opening 121 of the pressurized cavity 12 in a moment, the pressurized cavity 12 feeds back an expiratory resistance. Therefore, the oscillation element 20 uses a cyclical effect of the forward thrust and the reverse thrust to produce a treatment of oscillating positive expiratory pressure (hereafter referred to as "OPEP").

Examples of a practicing manner of the indicator element 50 will be illustrated below, in a first practicing manner of the indicator element 50, the indicator element 50 is integrally formed on the first end 23 of the oscillation element 20, and thereby to simplify the structure. In a second practicing manner of the indicator element 50, the indicator element 50 is made of a flexible material, the indicator element 50 is fixed on the first end 23 of the oscillation element 20, and thereby to increase the amplitude of the indicator element 50.

Examples of a protecting manner of the indicator element 50 of the first preferred embodiment will be illustrated below, a top portion 11 of the shell 10 has a transparent window 70, the transparent window 70 is located above the indicator element 50, an oscillating state of the oscillation element 20 is indicated by the indicator element 50, the oscillating state of the oscillation element 20 can be displayed from the transparent window 70, that will feed back a visual incentive effect to a user, and thereby increasing the success of OPEP therapy.

Examples of a conspicuous manner of the indicator element 50 will be illustrated below, the indicator element 50 is provided with different color intervals or patterns, and thereby to increase the conspicuous effect of the indicator element 50 which is in an oscillating state. Moreover, the indicator element 50 can be made of a bright-colored material or a fluorescent material, and thereby to increase the conspicuous effect of the indicator element 50 which is in an oscillating state.

Examples of an oscillation direction of the oscillation element 20 will be illustrated below, the oscillation element 20 oscillates relative to a wall surface 14 of the shell 10, which is an oscillation direction d1 of the first preferred embodiment. The pressurized cavity 12 is located on the wall surface 14, a pivot 25 of the oscillation element 20 is pivoted with a pair of pivot portions 15 of the wall surface 14.

Referring to FIGS. 3 to 6A, examples of an exhaust manner of the first preferred embodiment will be illustrated below, the shell 10 has a plurality of exhaust orifices 19, the exhaust orifices 19 are located above the pressurized cavity 12. Examples of the forming manner of the pressurized cavity 12 will be illustrated below, the pressurized cavity 12 further has a cover body 122, the cover body 122 can be fixed on the shell 10, and therefore the shell 10 can be easy to manufacture. Examples of the forming manner of the shell 10, the shell 10 is consisted of a left housing 101 and a right housing 102, the pressurized cavity 12 and the wall surface 14 are located at the left housing 101, the exhaust orifices 19 are located at the right housing 102, and therefore the shell 10 can be easy to manufacture.

Figure 5:
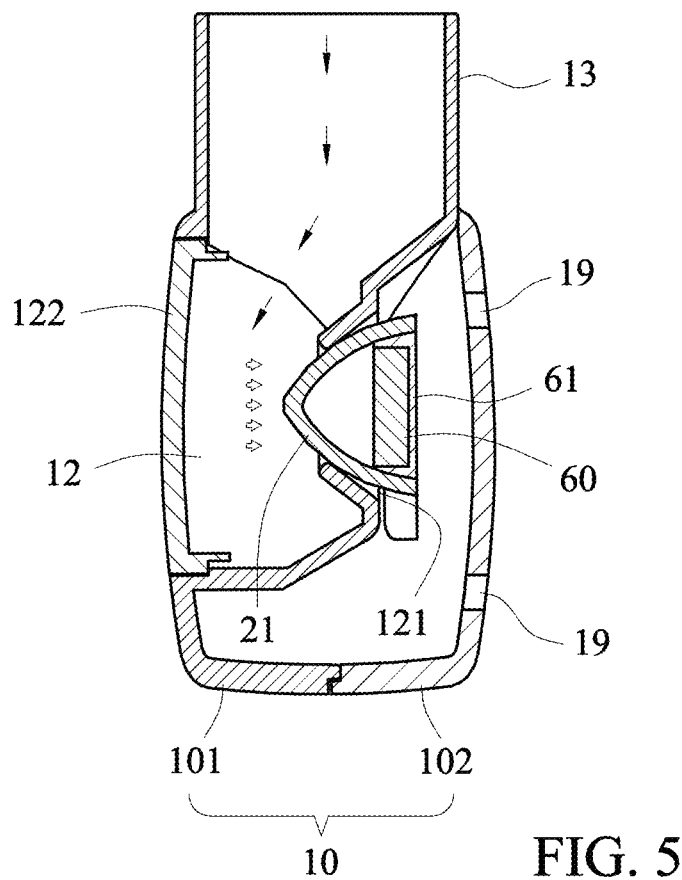
FIG. 5 is a partial cross-sectional perspective view along a line A-A of FIG. 2.
Figure 6A:
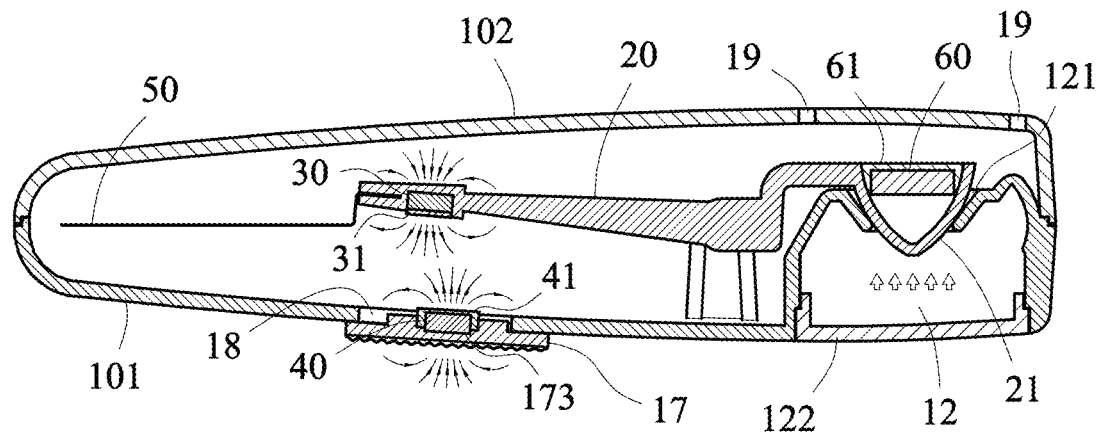
FIG. 6A is a cross-sectional view along a line B-B of FIG. 2.
Figure 6B:
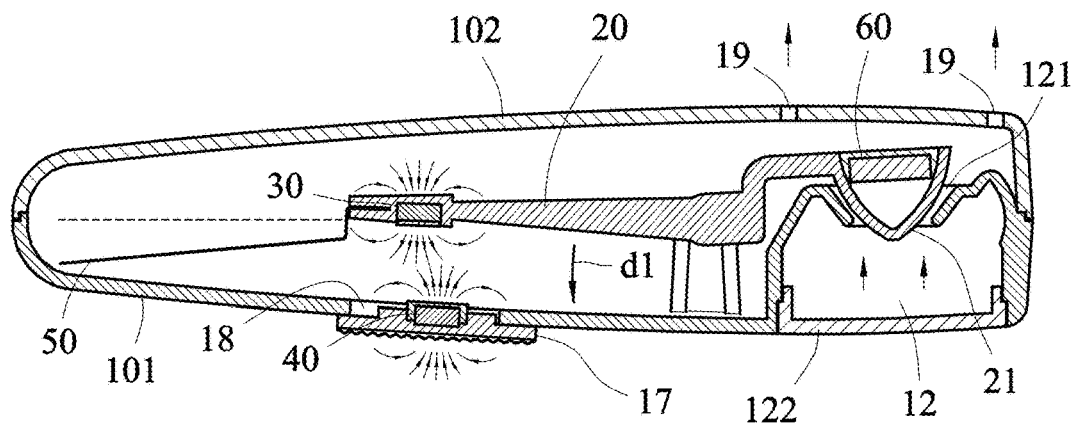
FIGS. 6B to 6D are low-frequency oscillation diagrams illustrating the first preferred embodiment of the invention.
Figure 6C:
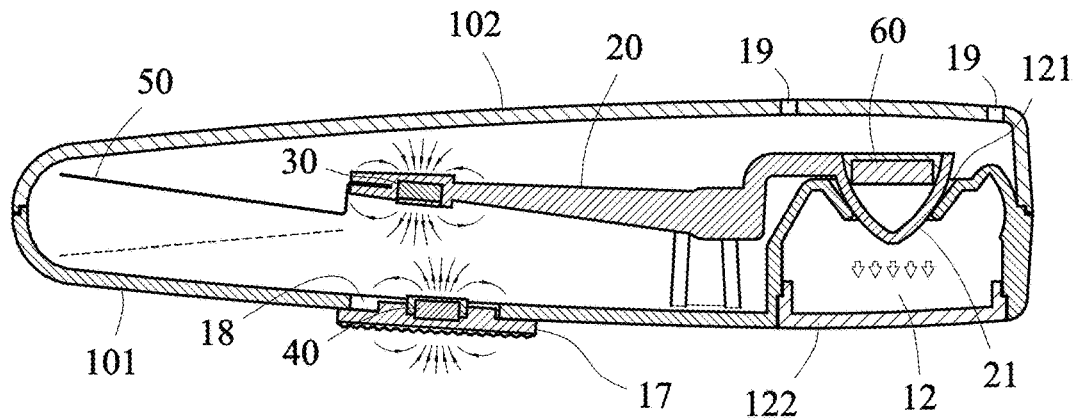
Figure 6D:
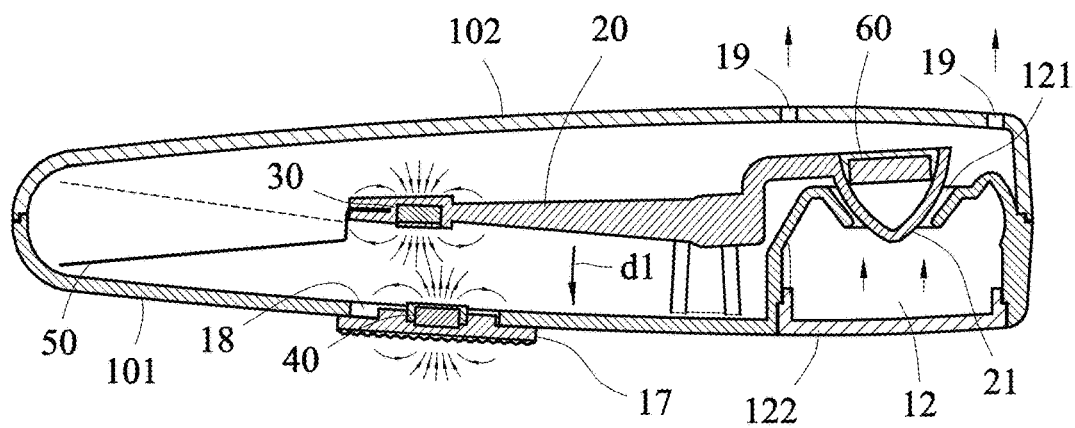

Referring to FIGS. 5 to 6D, examples of an oscillation process of positive expiratory pressure of the first preferred embodiment will be illustrated below. When the oscillation element 20 is in a static state, the valve 21 uses a repulsive force of the same poles to tend to close an opening 121 of the pressurized cavity 12, wherein the repulsive force is generated between the first magnetic element 30 and the second magnetic element 40. When an expiratory airflow enters the pressurized cavity 12 by the air inlet portion 13, the pressure of the pressurized cavity 12 rises instantaneously and generates a forward thrust to drive the oscillation element 20 to rotate (as shown in FIG. 5 and FIG. 6A). When the valve 21 separates from the opening 121 of the pressurized cavity 12 in a moment, the pressure of the pressurized cavity 12 is reduced instantaneously, the expiratory airflow uses the exhaust orifices 19 of the shell 10 to exhaust out, and therefore a reverse thrust will drives the oscillation element 20 to return to an original position, wherein the reverse thrust is generated by the first magnetic element 30 and the second magnetic element 40 (as shown in FIG. 6B). When the valve 21 closes the opening 121 of the pressurized cavity 12 in a moment, the pressure of the pressurized cavity 12 will rises again, the pressurized cavity 12 feeds back an expiratory resistance (as shown in FIG. 6C). When the valve 21 separates from the opening 121 of the pressurized cavity 12 in a moment, the pressure of the pressurized cavity 12 is reduced instantaneously, the expiratory airflow uses the exhaust orifices 19 of the shell 10 to exhaust out, and therefore a reverse thrust will drives the oscillation element 20 to return to an original position, wherein the reverse thrust is generated by the first magnetic element 30 and the second magnetic element 40 (as shown in FIG. 6D). Thus, the oscillation element 20 and the pressurized cavity 12 can produces the oscillating positive expiratory pressure by a cyclical process of FIG. 6C and FIG. 6D.

Figure 7A:
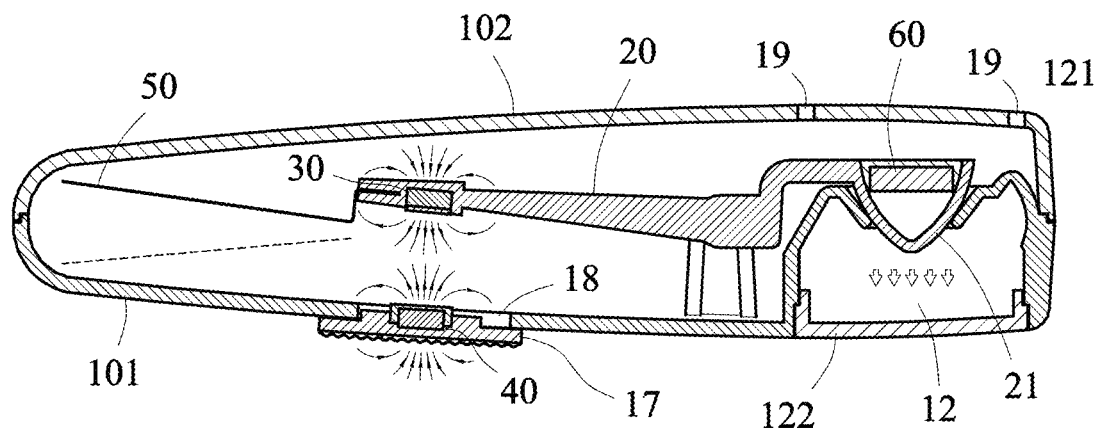
FIGS. 7A to 7B are high-frequency oscillation diagrams illustrating the first preferred embodiment of the invention.
Figure 7B:
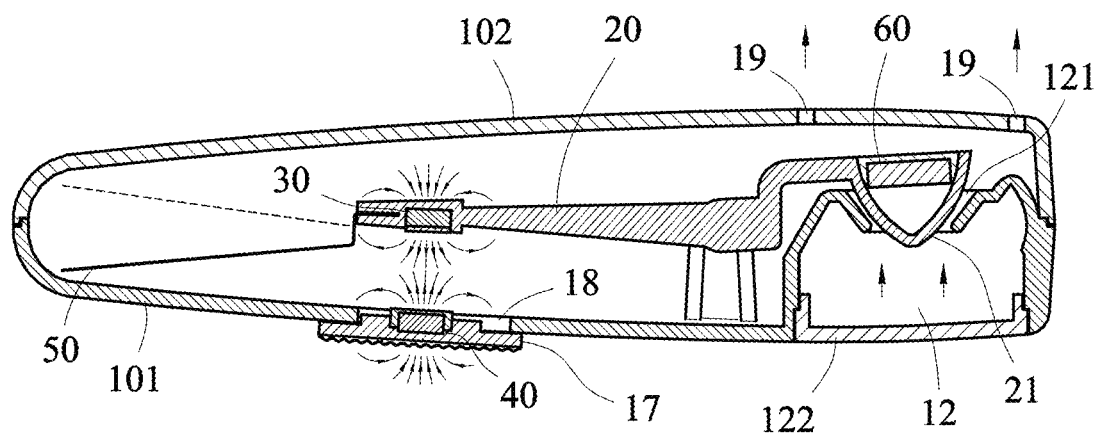
Figure 8A:
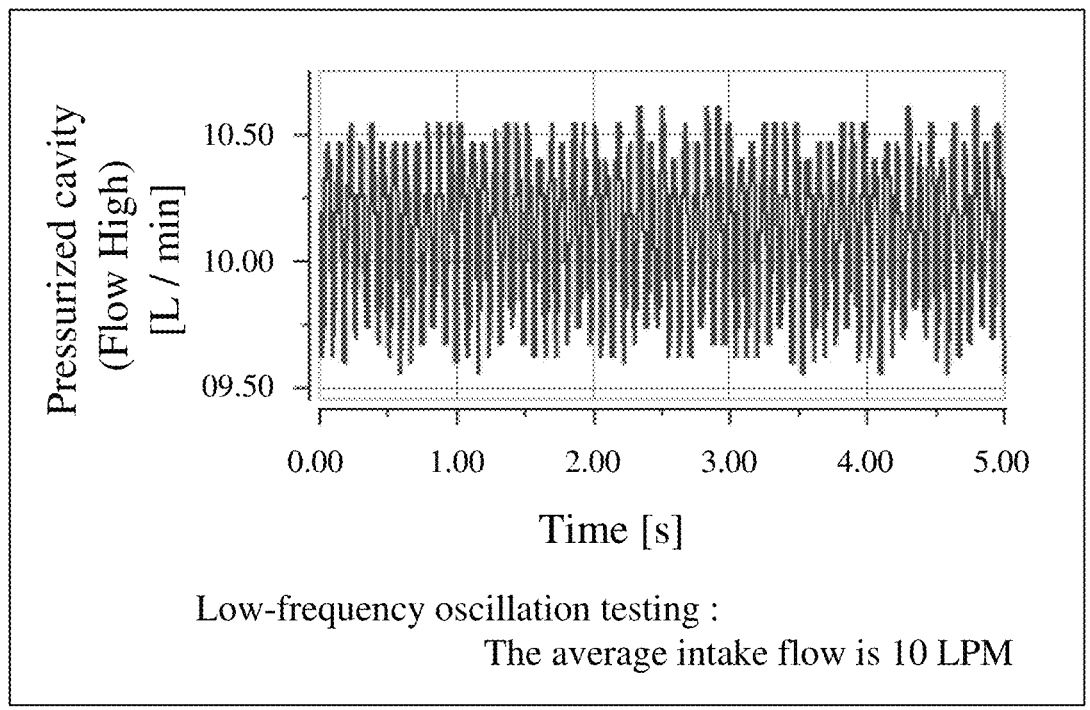
FIGS. 8A to 8B are first charts illustrating a low-frequency test record of the invention.
Figure 8B:
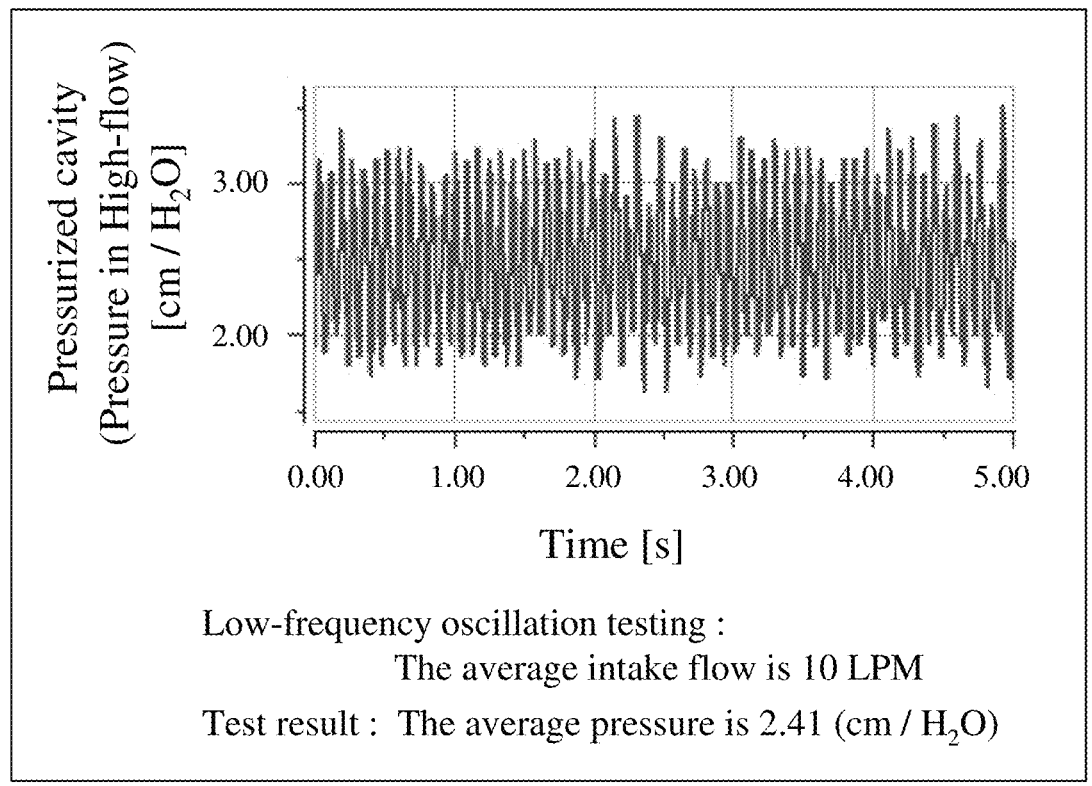
Figure 9A:
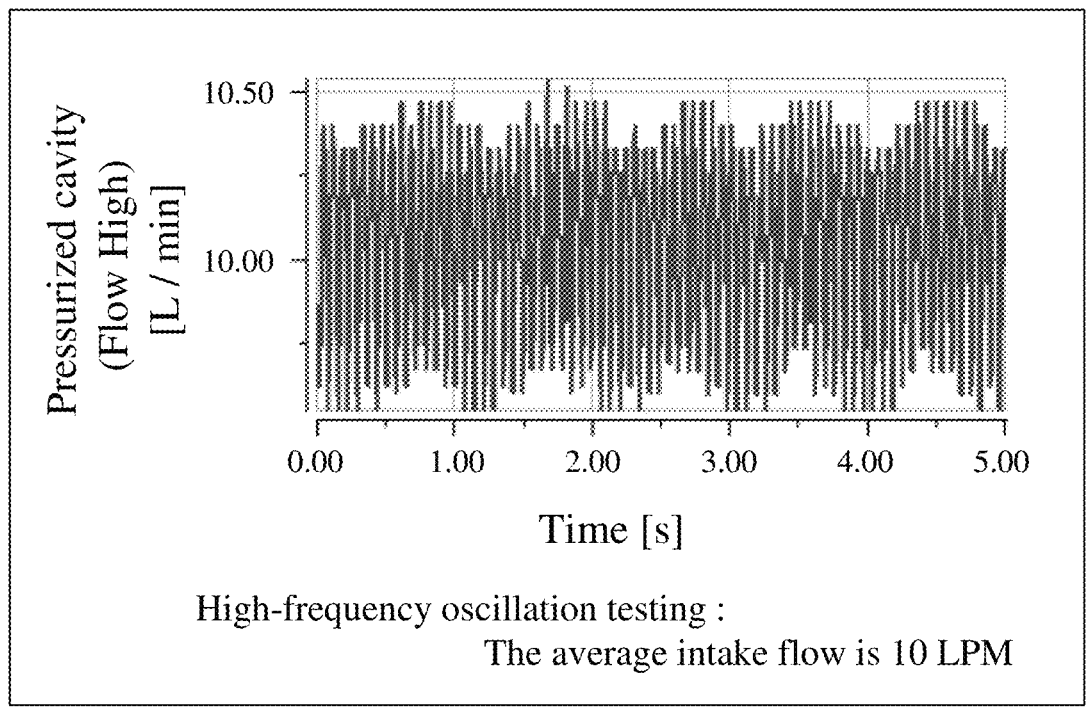
FIGS. 9A to 9B are first charts illustrating a high-frequency test record of the invention.
Figure 9B:
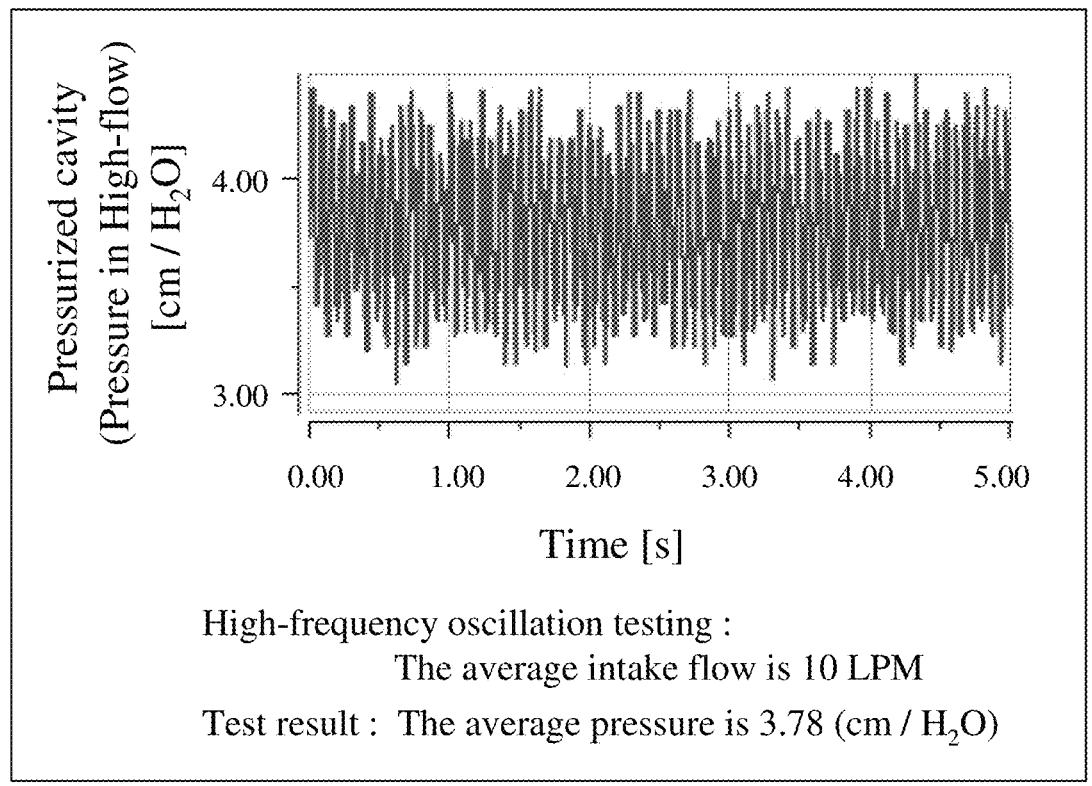
Figure 10A:
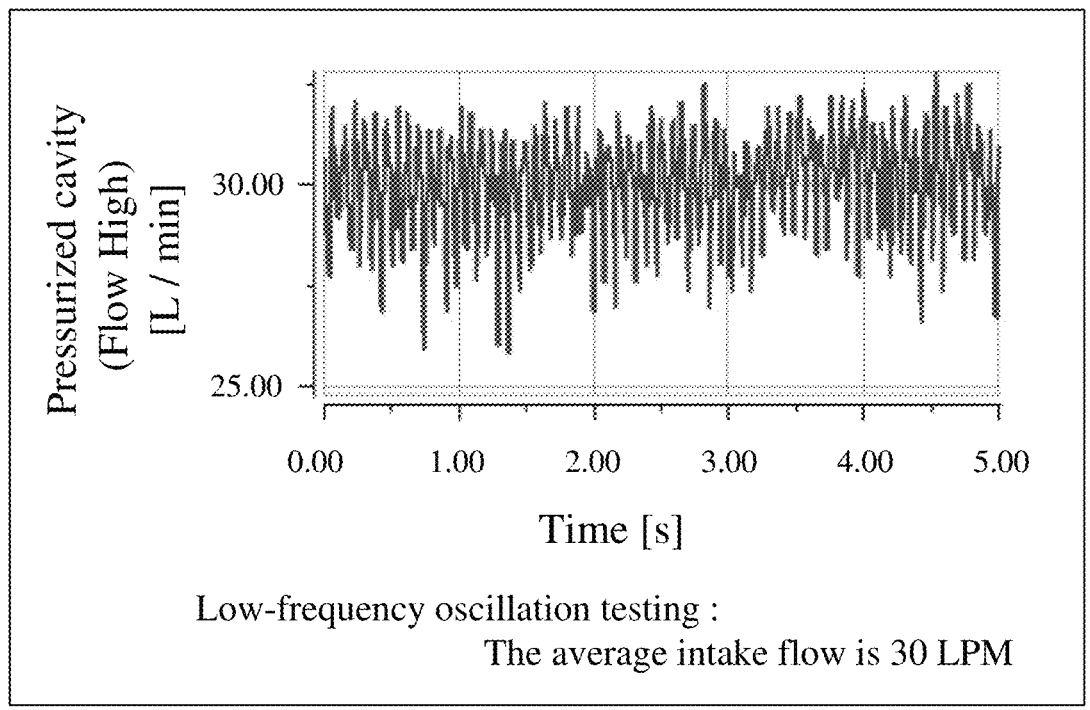
FIGS. 10A to 10B are second charts illustrating a low-frequency test record of the invention.
Figure 10B:
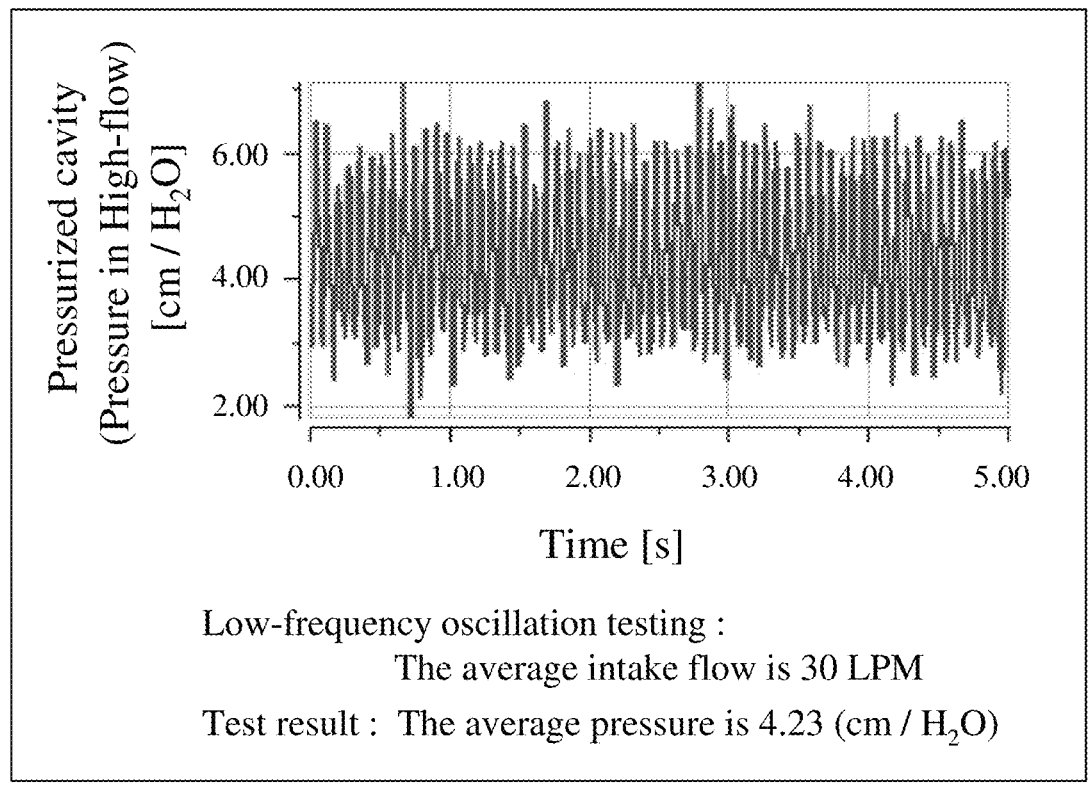
Figure 11A:
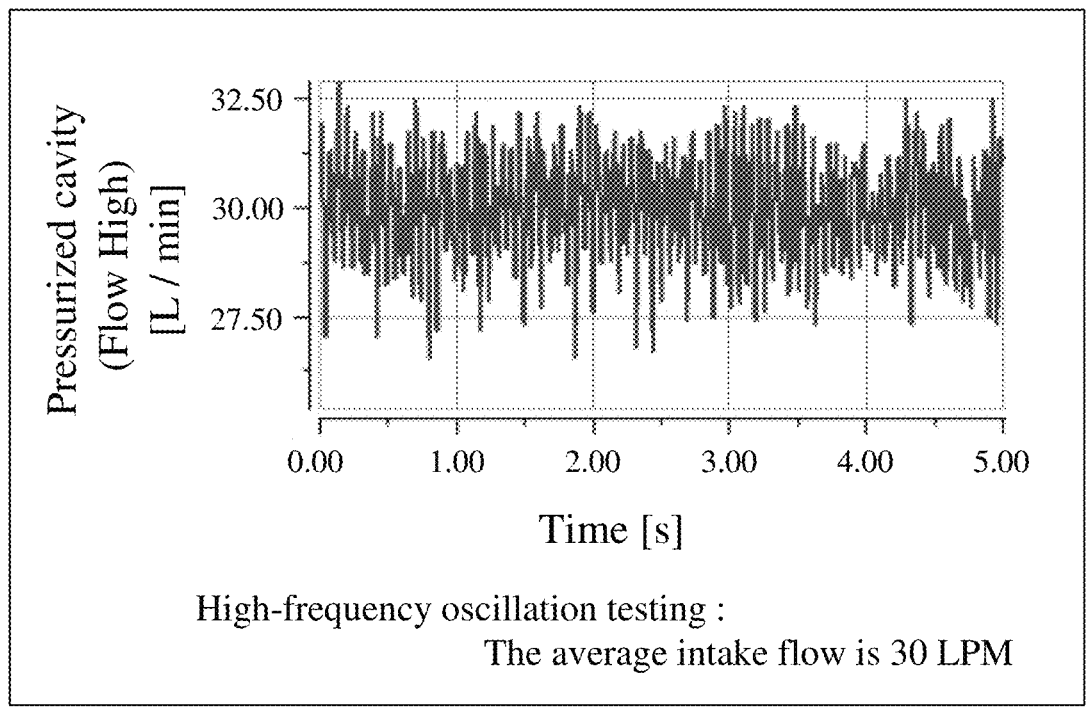
FIGS. 11A to 11B are second charts illustrating a high-frequency test record of the invention.
Figure 11B:
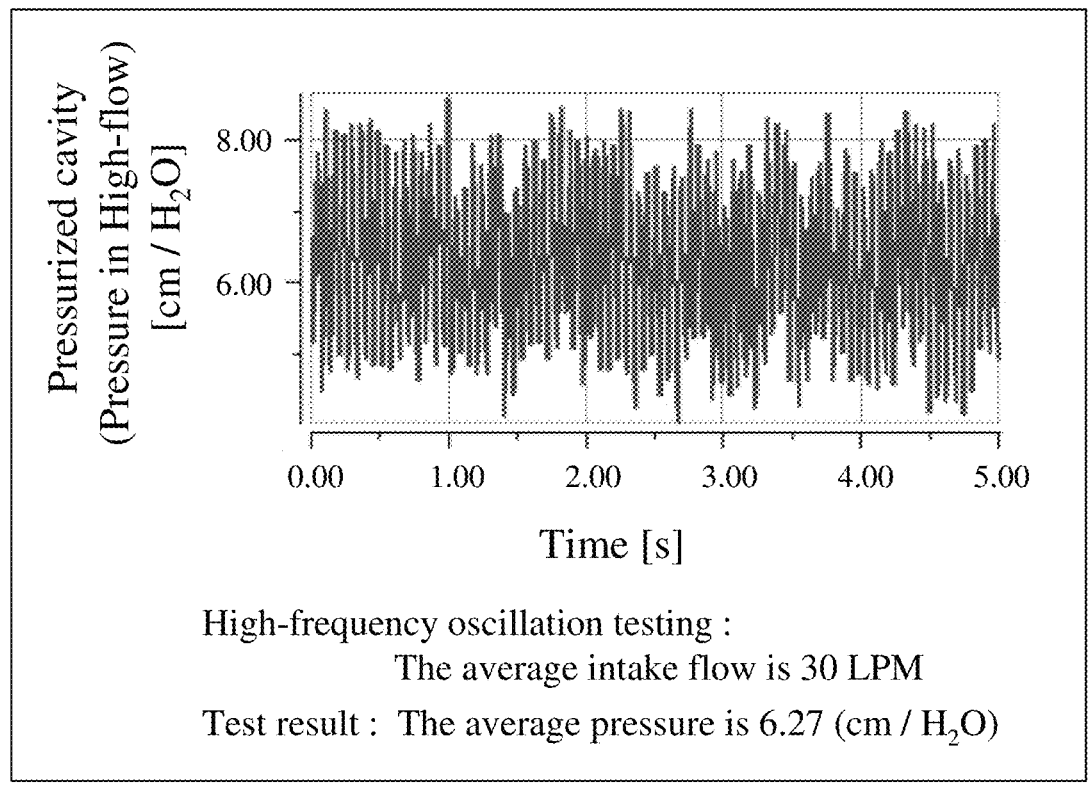
Figure 12:
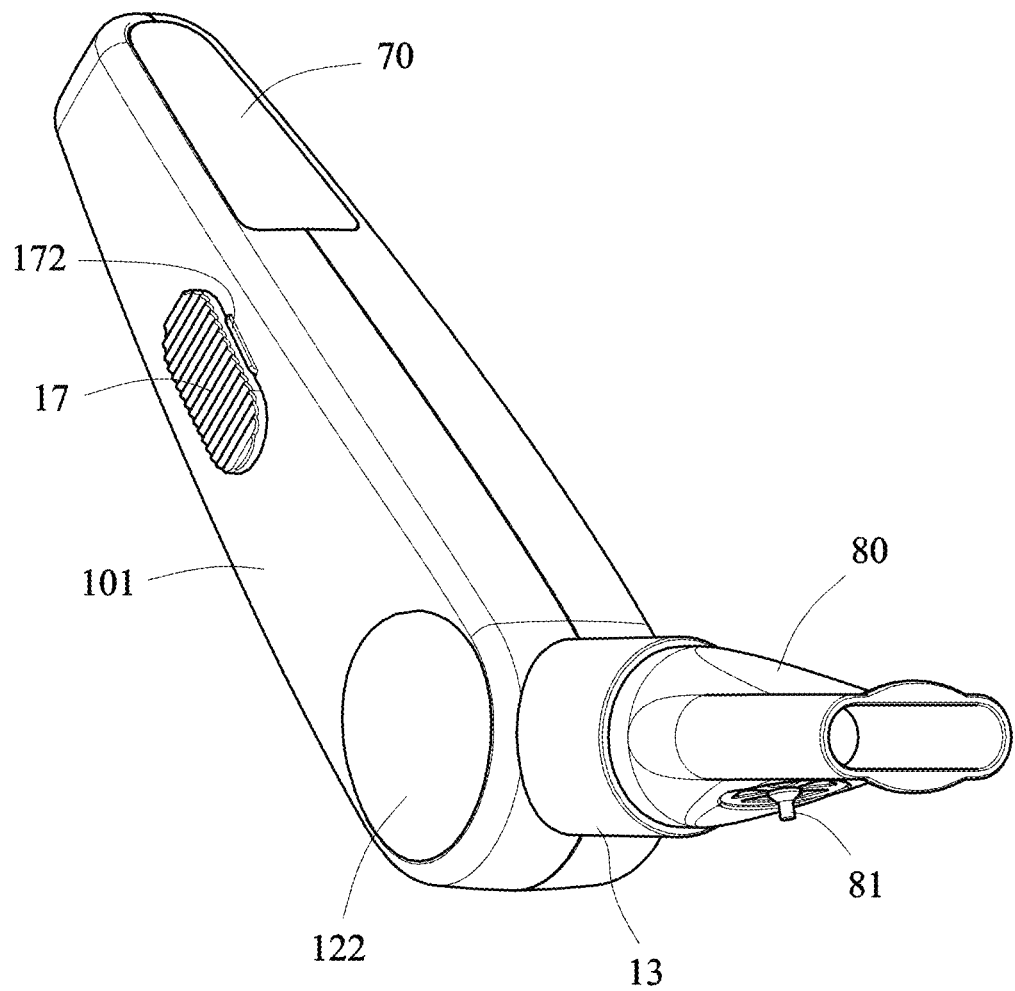
FIG. 12 is a diagram illustrating the first preferred embodiment of the invention connected with a mouthpiece element.
Figure 13:
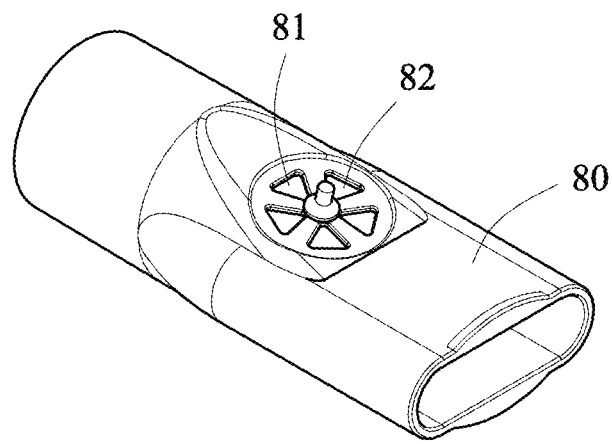
FIG. 13 is a perspective view showing the mouthpiece element of the invention.
Figure 14:
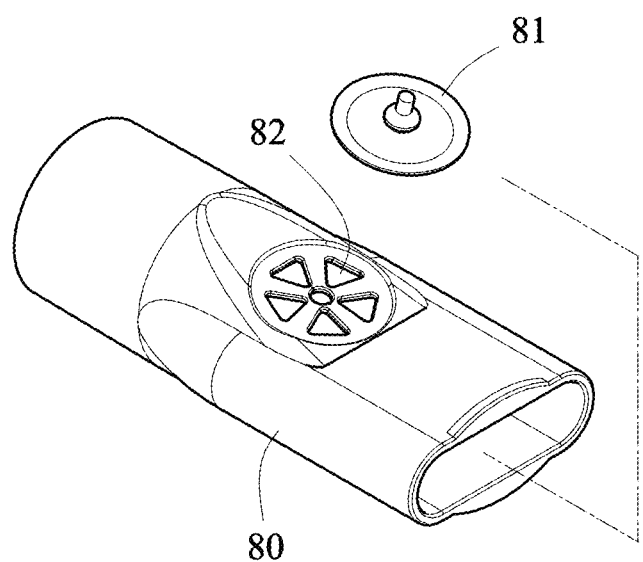
FIG. 14 is an exploded view showing the mouthpiece element of the invention.

Referring to FIGS. 3 to 7B, examples of an oscillation adjusting manner of the oscillation element 20 will be illustrated below. In a first adjusting manner, a counterweight element 60 is disposed on a second end 26 of the oscillation element 20 to balance a moment formed by the weight of the first magnetic element 30. In a second adjusting manner, the shell 10 further has a sliding seat 17 and a slot 18, the second magnetic element 40 is disposed on the sliding seat 17, the sliding seat 17 can slides along the slot 18 thereby moving the position of the second magnetic element 40. When the position of the second magnetic element 40 is close to the position of the first magnetic element 30, a reverse thrust (i.e. a repulsive force of the same poles) will be increased, wherein the reverse thrust is formed between the first magnetic element 30 and the second magnetic element 40, and therefore the oscillation element 20 can generates a high-frequency oscillation of positive expiratory pressure (as shown in FIG. 7A and FIG. 7B). When the position of the second magnetic element 40 is far away from the position of the first magnetic element 30, the reverse thrust (i.e. a repulsive force of the same poles) will be weakened, wherein the reverse thrust is formed between the first magnetic element 30 and the second magnetic element 40, and therefore the oscillation element 20 can generates a low-frequency oscillation of positive expiratory pressure (as shown in FIG. 6C and FIG. 6D). Thus, the oscillating frequency of the oscillation element 20 can be adjusted by moving the position of the sliding seat 17, and further to adjust the expiratory resistance which is formed by the valve 21 and the pressurized cavity 12.

Examples of a combination manner of the sliding seat 17 and the slot 18 will be illustrated below, the sliding seat 17 has a plurality of hooks 171, the sliding seat 17 uses the hooks 171 to buckle the slot 18, the shell 10 has a plurality of ribs 172 adjacent to the slot 18, wherein the hooks 171 and the ribs 172 can be used as a sliding mechanism of the sliding seat 17, and therefore the sliding seat 17 can be moved along the slot 18.

Examples of a protecting manner of the first magnetic element 30 and the second magnetic element 40 will be illustrated below, the first magnetic element 30 is further fixed on the first end 23 of the oscillation element 20 by a package body 31 (for example, a fixing glue, a sealant, or any packaging material is complied with the use of medical device); the second magnetic element 40 is further fixed on a recess 173 of the sliding seat 17 by a package body 41 (for example, a fixing glue, a sealant, or any packaging material is complied with the use of medical device). Examples of a protecting manner of the counterweight element 60 will be illustrated below, the counterweight element 60 is further fixed on the second end 26 of the oscillation element 20 by a package body 61 (for example, a fixing glue, a sealant, or any packaging material is complied with the use of medical device).

Referring to FIGS. 6C, 6D, 8A and 8B, examples of a low-frequency oscillation testing of the oscillation element 20 and the pressurized cavity 12 will be illustrated below. The position of the second magnetic element 40 can be farthest from the position of the first magnetic element 30 by moving the position of the sliding seat 17, an airflow of a gas source device (not shown) is used to test a flow rate and a pressure of the pressurized cavity 12 in high-flow, wherein the average intake flow is 10 LPM (L/min). In the FIG. 8A, a horizontal axis is a time axis (e.g. the unit of the time axis is the second), a vertical axis is a flow axis (e.g. the unit of the flow axis is the LPM), an oscillating change of flow rate of the pressurized cavity 12 is about between 09.60 LPM and 10.70 LPM. In the FIG. 8B, a horizontal axis is a time axis (e.g. the unit of the time axis is the second), a vertical axis is a pressure axis (e.g. the unit of the pressure axis is the cm/H$_2$O), an oscillating change of pressure of the pressurized cavity 12 is about between 1.60 (cm/H$_2$O) and 3.50 (cm/H$_2$O), wherein the average pressure is 2.41 (cm/H$_2$O).

Referring to FIGS. 7A, 7B, 9A and 9B, examples of a high-frequency oscillation testing of the oscillation element 20 and the pressurized cavity 12 will be illustrated below. The position of the second magnetic element 40 can be farthest from the position of the first magnetic element 30 by moving the position of the sliding seat 17, an airflow of a gas source device (not shown) is used to test a flow rate and a pressure of the pressurized cavity 12 in high-flow, wherein the average intake flow is 10 LPM (L/min). In the FIG. 9A, a horizontal axis is a time axis (e.g. the unit of the time axis is the second), a vertical axis is a flow axis (e.g. the unit of the flow axis is the LPM), an oscillating change of flow rate of the pressurized cavity 12 is about between 09.50 LPM and 10.60 LPM. In the FIG. 9B, a horizontal axis is a time axis (e.g. the unit of the time axis is the second), a vertical axis is a pressure axis (e.g. the unit of the pressure axis is the cm/H$_2$O), an oscillating change of pressure of the pressurized cavity 12 is about between 3.00 (cm/H$_2$O) and 4.50 (cm/H$_2$O), wherein the average pressure is 3.78 (cm/H$_2$O).

Referring to FIGS. 6C, 6D, 10A and 10B, examples of a low-frequency oscillation testing of the oscillation element 20 and the pressurized cavity 12 will be illustrated below. The position of the second magnetic element 40 can be farthest from the position of the first magnetic element 30 by moving the position of the sliding seat 17, an airflow of a gas source device (not shown) is used to test a flow rate and a pressure of the pressurized cavity 12 in high-flow, wherein the average intake flow is 30 LPM (L/min). In the FIG. 10A, a horizontal axis is a time axis (e.g. the unit of the time axis is the second), a vertical axis is a flow axis (e.g. the unit of the flow axis is the LPM), an oscillating change of flow rate of the pressurized cavity 12 is about between 25.30 LPM and 30.50 LPM. In the FIG. 10B, a horizontal axis is a time axis (e.g. the unit of the time axis is the second), a vertical axis is a pressure axis (e.g. the unit of the pressure axis is the cm/H$_2$O), an oscillating change of pressure of the pressurized cavity 12 is about between 1.90 (cm/H$_2$O) and 6.50 (cm/H$_2$O), wherein the average pressure is 4.23 (cm/H$_2$O).

Referring to FIGS. 7A, 7B, 11A and 11B, examples of a high-frequency oscillation testing of the oscillation element 20 and the pressurized cavity 12 will be illustrated below. The position of the second magnetic element 40 can be farthest from the position of the first magnetic element 30 by moving the position of the sliding seat 17, an airflow of a gas source device (not shown) is used to test a flow rate and a pressure of the pressurized cavity 12 in high-flow, wherein the average intake flow is 30 LPM (L/min). In the FIG. 11A, a horizontal axis is a time axis (e.g. the unit of the time axis is the second), a vertical axis is a flow axis (e.g. the unit of the flow axis is the LPM), an oscillating change of flow rate of the pressurized cavity 12 is about between 26.50 LPM and 32.90 LPM. In the FIG. 11B, a horizontal axis is a time axis (e.g. the unit of the time axis is the second), a vertical axis is a pressure axis (e.g. the unit of the pressure axis is the cm/H$_2$O), an oscillating change of pressure of the pressurized cavity 12 is about between 4.00 (cm/H$_2$O) and 8.90 (cm/H$_2$O), wherein the average pressure is 6.27 (cm/H$_2$O).

Figure 15A:
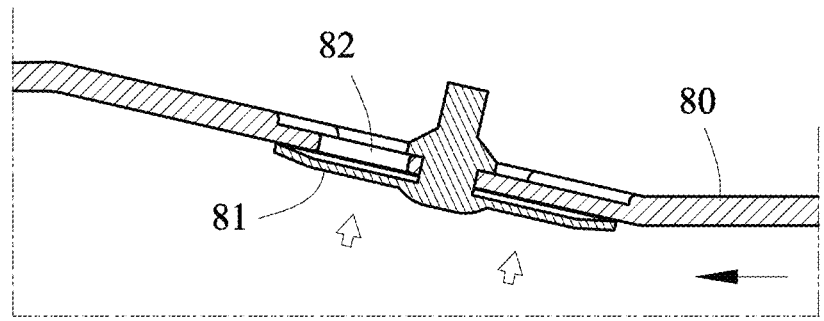
FIGS. 15A to 15B are action diagrams illustrating of an one-way valve of the invention.
Figure 15B:
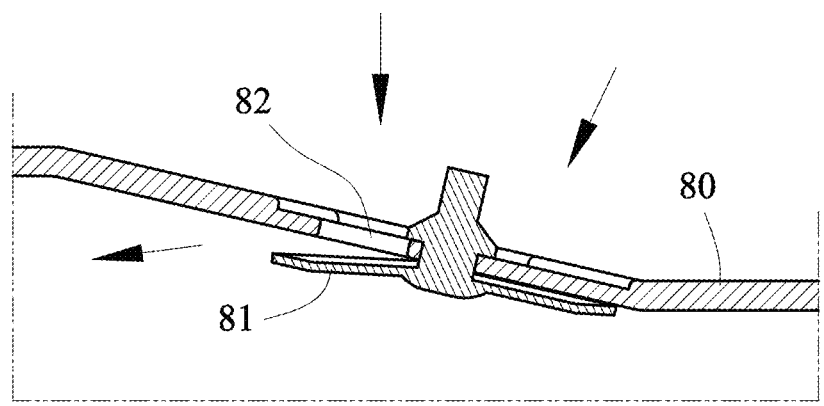

Referring to FIGS. 12 to 15B, examples of an air intake manner of the oscillation element 20 will be illustrated below. The air inlet portion 13 is further connected with a mouthpiece element 80, the mouthpiece element 80 has a one-way valve plate 81 and at least one air intake orifice 82, the one-way valve plate 81 is located inside the air intake orifice 82. When the user exhales through the mouthpiece element 80, the air intake orifice 82 can be closed by the one-way valve plate 81 (as shown in FIG. 15A). When the user inhales through the mouthpiece element 80, the one-way valve plate 81 opens the air intake orifice 82, the user can sucks air through the mouthpiece element 80 (as shown in FIG. 15B), and thereby to execute the following exhalation.

Figure 16:
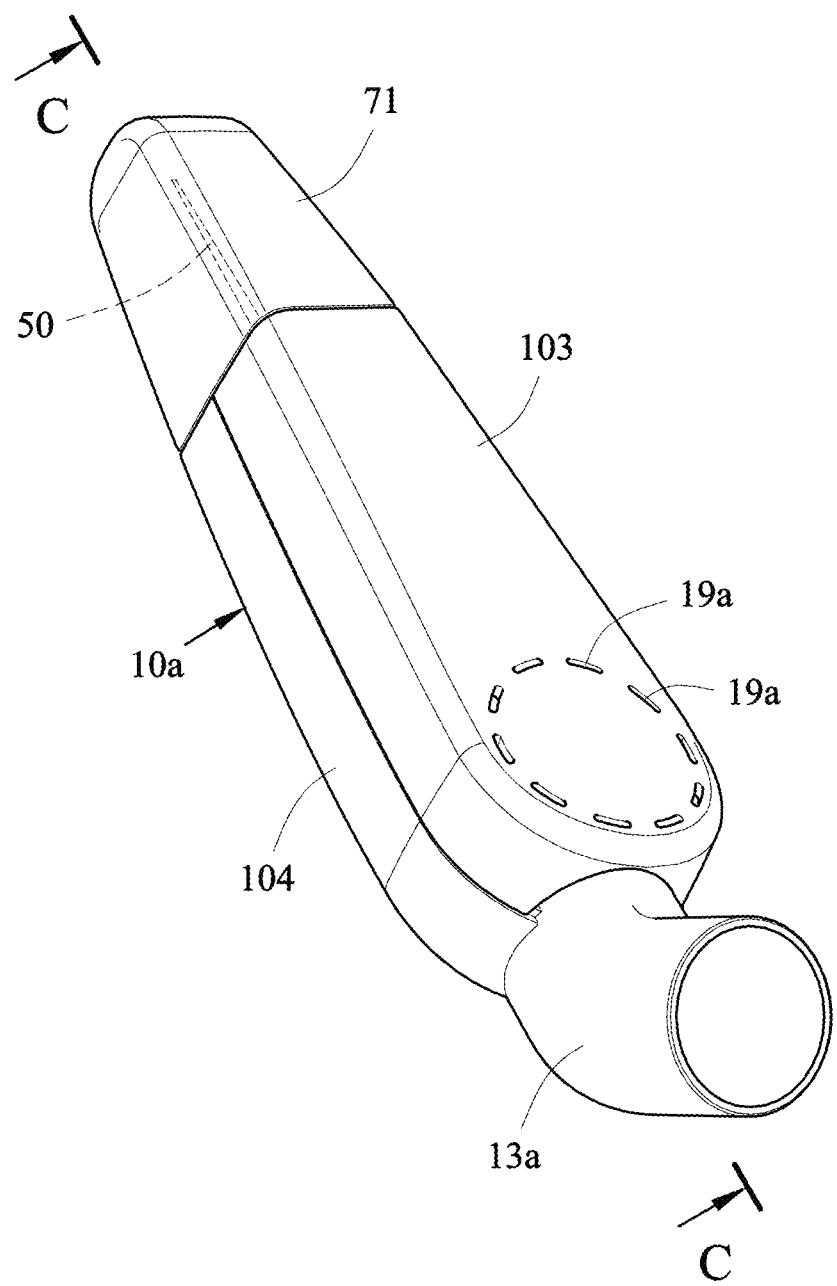
FIG. 16 is a perspective view showing a second preferred embodiment of the invention.
Figure 17:
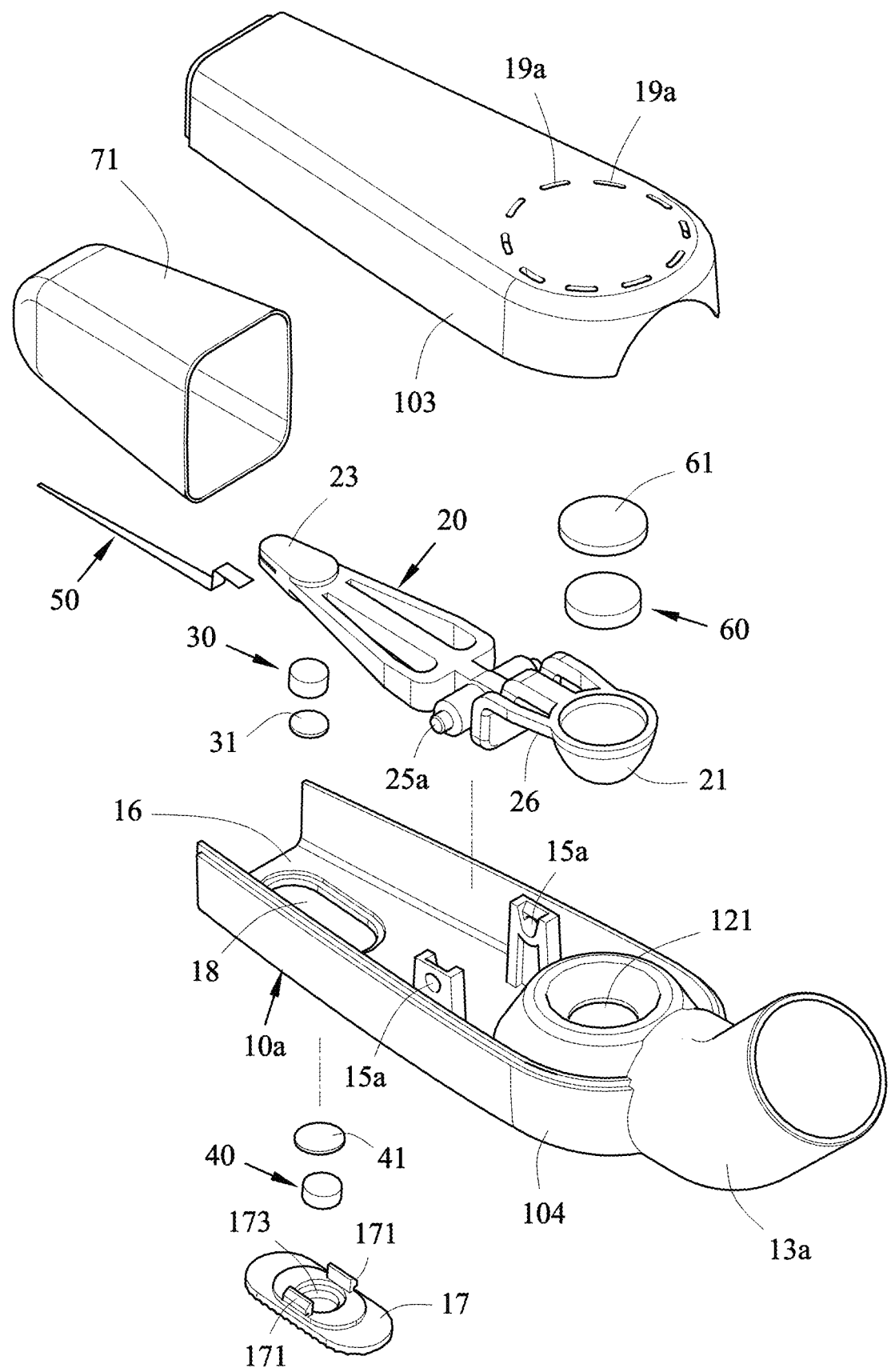
FIG. 17 is an exploded view showing the second preferred embodiment of the invention.
Figure 18:
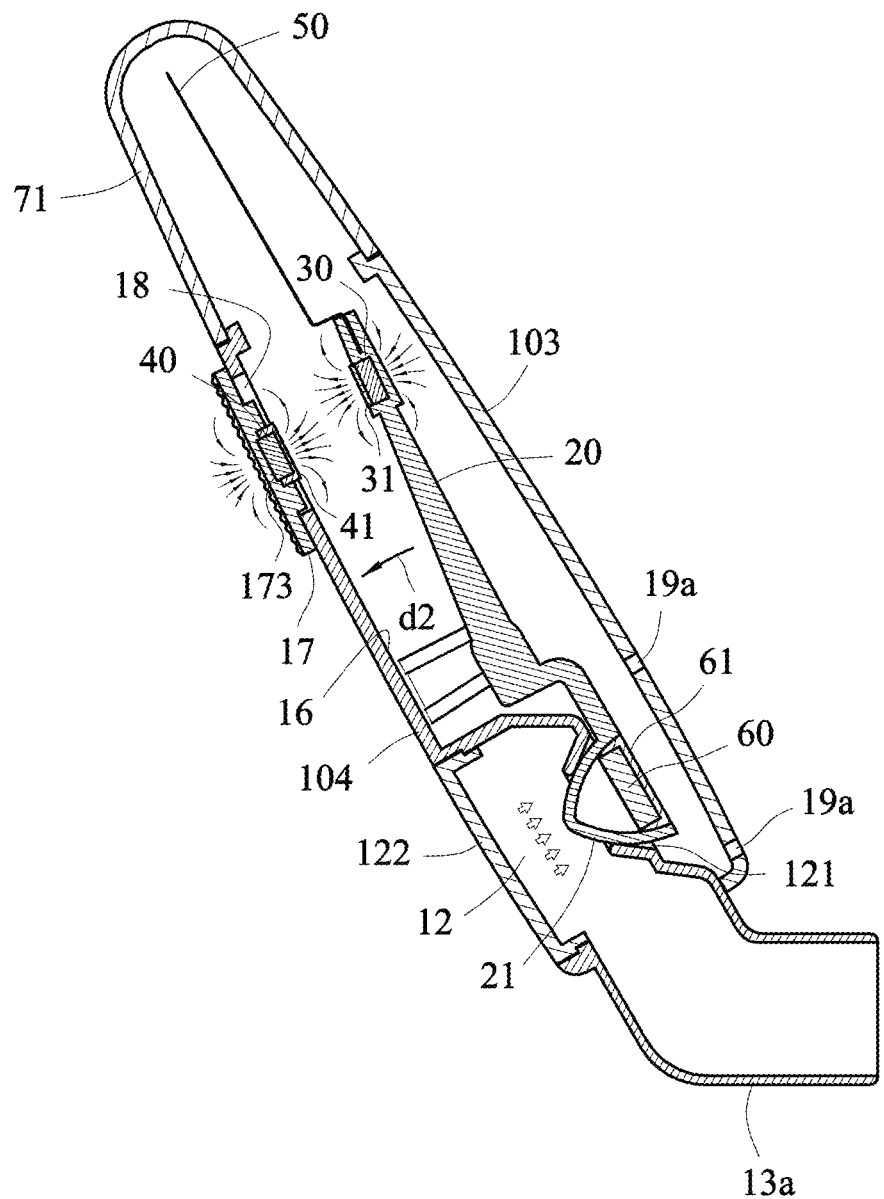
FIG. 18 is a cross-sectional view along a line C-C of FIG. 16.

Referring to FIGS. 16 to 18, a second embodiment of the invention is almost same as the first preferred embodiment, the difference between them is, the oscillation element 20 oscillates relative to a bottom portion 16 of the shell 10a, which is an oscillation direction d2 of the second embodiment; wherein the pressurized cavity 12 is located on the bottom portion 16, a pivot 25a of the oscillation element 20 is pivoted with a pair of pivot portions 15a of the bottom portion 16. Moreover, the shell 10a has a transparent cover 71 to contain the indicator element 50, which is a protecting manner of the indicator element 50 of the second embodiment; wherein an oscillating state of the oscillation element 20 is indicated by the indicator element 50, and therefore the oscillating state of the oscillation element 20 can be displayed from the transparent cover 71, that will feed back a visual incentive effect to a user, and thereby increasing the accurateness of OPEP therapy. Furthermore, the pressurized cavity 12 of the second embodiment is in fluid communication with a curved inlet portion 13a, and thereby to form a better angle of using.

Referring to FIGS. 16 to 18, examples of an exhaust manner of the second embodiment will be illustrated below, the shell 10a has a plurality of exhaust orifices 19a, the exhaust orifices 19a are located above the pressurized cavity 12. Examples of the forming manner of the pressurized cavity 12 will be illustrated below, the pressurized cavity 12 further has a cover body 122, the cover body 122 can be fixed on the shell 10a, and therefore the shell 10a can be easy to manufacture. Examples of the forming manner of the shell 10a, the shell 10a is consisted of a upper housing 103 and a lower housing 104, the pressurized cavity 12 and the wall surface 14 are located at the lower housing 104, the exhaust orifices 19a are located at the upper housing 103, and therefore the shell 10a can be easy to manufacture.

What is claimed is:

1. A portable oscillator of positive expiratory pressure having capability for oscillating indication, the portable oscillator of positive expiratory pressure comprising:
    a shell, the shell has a pressurized cavity in fluid communication to an air inlet portion;
    an oscillation element pivoting in the shell, the oscillation element has a valve;
    a first magnetic element disposed on a first end of the oscillation element;
    a second magnetic element disposed on the shell, the magnetic field lines of the first magnetic element in a direction opposite to the direction of the magnetic field lines of the second magnetic element, and therefore the valve tends to close an opening of the pressurized cavity;
    an indicator element located at the first end of the oscillation element;
    wherein an expiratory airflow generates a forward thrust in the pressurized cavity to drive the oscillation element to rotate, and therefore a distance between the first magnetic element and the second magnetic element is shortened to generate a reverse thrust; when the valve separates from the opening of the pressurized cavity in a moment, the forward thrust is reduced, and therefore the reverse thrust can drives the oscillation element to return to an original position; when the valve closes the opening of the pressurized cavity in a moment, the pressurized cavity feeds back an exhalation resistance; and therefore the oscillation element produces an oscillating positive expiratory pressure by a cyclical effect of the forward thrust and the reverse thrust; and
    wherein the shell further has a slot defined through a side wall of the shell and extending in a lengthwise direction of the shell, and a sliding seat slidably disposed in the slot, the sliding seat having a sliding mechanism exposed to an outside of the shell, wherein the second magnetic element is disposed on the sliding seat at a position within the shell, whereby the sliding seat can slide along the slot thereby moving the position of the second magnetic element in the lengthwise direction of the shell and transverse to the first magnetic element.

2. The portable oscillator of positive expiratory pressure having capability for oscillating indication of claim 1, wherein the indicator element is integrally formed on the first end of the oscillation element, the first magnetic element is further fixed on the first end of the oscillation element by a package body.

3. The portable oscillator of positive expiratory pressure having capability for oscillating indication of claim 1, wherein the indicator element is made of a flexible material, the indicator element is fixed on the first end of the oscillation element, the first magnetic element is further fixed on the first end of the oscillation element by a package body.

4. The portable oscillator of positive expiratory pressure having capability for oscillating indication of claim 1, wherein a top portion of the shell has a transparent window, the transparent window is located above the indicator element, an oscillating state of the oscillation element is indicated by the indicator element, and therefore the oscillating state of the oscillation element can be displayed from the transparent window.

5. The portable oscillator of positive expiratory pressure having capability for oscillating indication of claim 1, wherein the shell further has a transparent cover to contain the indicator element, an oscillating state of the oscillation element is indicated by the indicator element, and therefore the oscillating state of the oscillation element can be displayed from the transparent cover.

6. The portable oscillator of positive expiratory pressure having capability for oscillating indication of claim 1, wherein the oscillation element oscillates relative to a wall surface of the shell, the pressurized cavity is located on the wall surface, a pivot of the oscillation element is pivoted with a pair of pivot portions of the wall surface.

7. The portable oscillator of positive expiratory pressure having capability for oscillating indication of claim 1, wherein the oscillation element oscillates relative to a bottom portion of the shell, the pressurized cavity is located on the bottom portion, a pivot of the oscillation element is pivoted with a pair of pivot portions of the bottom portion.

8. The portable oscillator of positive expiratory pressure having capability for oscillating indication of claim 1, wherein a counterweight element is disposed on a second end of the oscillation element to balance a moment formed by the weight of the first magnetic element, the counterweight element is further fixed on the second end of the oscillation element by a package body.

9. The portable oscillator of positive expiratory pressure having capability for oscillating indication of claim 1, wherein the shell has a plurality of exhaust orifices, the exhaust orifices are located above the pressurized cavity; the air inlet portion is further connected with a mouthpiece element, the mouthpiece element has a one-way valve plate and at least one air intake orifice, the one-way valve plate is located inside the air intake orifice; when exhaling, the air intake orifice can be closed by the one-way valve plate; when inhaling, the one-way valve plate opens the air intake orifice to inhale.

10. A portable oscillator of positive expiratory pressure having capability for oscillating indication, the portable oscillator of positive expiratory pressure comprising:
  a shell, the shell has a pressurized cavity in fluid communication to an air inlet portion;
  an oscillation element pivoting in the shell, the oscillation element has a valve;
  a first magnetic element disposed on a first end of the oscillation element;
  a second magnetic element supported on the shell and positioned and arranged to move along a wall of the shell and in a lengthwise direction of the shell and transverse to said first magnetic element, wherein the magnetic field lines of the first magnetic element in a direction opposite to the direction of the magnetic field lines of the second magnetic element, and therefore the valve tends to close an opening of the pressurized cavity;
  an indicator element located at the first end of the oscillation element;
  wherein an expiratory airflow generates a forward thrust in the pressurized cavity to drive the oscillation element to rotate, and therefore a distance between the first magnetic element and the second magnetic element is shortened to generate a reverse thrust; when the valve separates from the opening of the pressurized cavity in a moment, the forward thrust is reduced, and therefore the reverse thrust can drives the oscillation element to return to an original position; when the valve closes the opening of the pressurized cavity in a moment, the pressurized cavity feeds back an exhalation resistance; and therefore the oscillation element produces an oscillating positive expiratory pressure by a cyclical effect of the forward thrust and the reverse thrust.

* * * * *